US007981639B2

(12) United States Patent
Shaw et al.

(10) Patent No.: US 7,981,639 B2
(45) Date of Patent: Jul. 19, 2011

(54) STARCH-DERIVED PRODUCTS

(75) Inventors: Jei-Fu Shaw, Taipei (TW); Guan-Chiun Lee, Taipei (TW); Jen-Jye Chen, Taichung (TW)

(73) Assignee: Academia Sinica, Taipei (TW)

( * ) Notice: Subject to any disclaimer, the term of this patent is extended or adjusted under 35 U.S.C. 154(b) by 489 days.

(21) Appl. No.: 10/782,287

(22) Filed: Feb. 19, 2004

(65) Prior Publication Data

US 2004/0161829 A1 Aug. 19, 2004

Related U.S. Application Data

(60) Provisional application No. 60/448,814, filed on Feb. 19, 2003.

(51) Int. Cl.
*A23L 1/105* (2006.01)
*C12G 1/022* (2006.01)

(52) U.S. Cl. ............. 435/96; 435/99; 435/161; 426/11; 426/28; 426/29

(58) Field of Classification Search .................... 435/96, 435/99, 161; 426/11, 28, 29
See application file for complete search history.

(56) References Cited

U.S. PATENT DOCUMENTS

| 3,551,293 | A | * | 12/1970 | Seidman et al. ............... 435/99 |
| 3,922,196 | A | * | 11/1975 | Leach et al. .................... 435/95 |
| 4,322,569 | A | | 3/1982 | Chao et al. |
| 4,861,381 | A | | 8/1989 | Paul et al. |
| 5,312,739 | A | | 5/1994 | Shaw |
| 5,512,464 | A | | 4/1996 | Spencer et al. |
| 6,455,301 | B1 | | 9/2002 | Lin et al. |
| 6,570,043 | B2 | | 5/2003 | Elliott et al. |
| 6,602,691 | B1 | | 8/2003 | Ojamo et al. |
| 2002/0132313 | A1 | | 9/2002 | Lin et al. |

FOREIGN PATENT DOCUMENTS

| JP | 02-076592 | | 3/1990 |
| JP | 2-76592 | | 3/1990 |
| JP | 8-154665 | | 6/1996 |
| JP | 9-9986 | | 1/1997 |
| JP | 10248562 | A * | 9/1998 |
| JP | 2002-17337 | | 1/2002 |
| JP | 2002-520066 | | 9/2002 |

OTHER PUBLICATIONS

Steinkraus. Classification of fermented foods: worldwide view of household fermentation techniques. 1997. Food Control. vol. 8:311-317 (p. 314).*
A-amylase and glucoamylase from *Aspergillus oryzae*, var. (http://www.fao.org/ag/agn/jecfa-additives/specs/Monograph1/Additive-028.pdf).*
Skory et al. 1997. Screening for ethanol-producing blamentous fungi. Biotechnology Letters, vol. 19, No. 3, Mar. 1997, pp. 203-206.*
Shaw et al. 1992. Production of high-maltose syrup and high-protein flour from rice by an enzymatic method. Biocsi. Biotech. Biochem. 56(7):1071-1073.*
Nutrition Facts of white glutinous rice. 2009. http://www.nutrientfacts.com/searchfood.exe?keyword=Rice+White+Glutinous+Raw&var=5. p. 1.*
Jones et al. 1927. The Globulins of Rice, *Oryza sativa*. J. Biol. Chem. 74:415-426.*
Javanainen et al. 1995. Lactic Acid Fermentation on Barley Flour Without Additional Nutrients. Biotechnology Techniques. vol. 9 No. 8. pp. 543-548.*
Cadmus et al. 1966. Enzymatic Production of Glucose Syrup From Grains and Its Use in Fermentations. Cereal Chem 43:658-669.*
Third Party comments regarding Japanese Publication No. 02-076592 (15 pages, English Translation, 18 pages; Verification of Translation, 1 page), Jan. 5, 2009.
Takasaki, Yoshiyuki, "Development of Thermostable and/or Acid Stable α-Amylase, Glucose Isomerase and Mannose Isomerase," Nippon Shokuhin Kagaku Kaishi, vol. 48, No. 2, p. 150-156 (2001).
Bhat, Mahalingeshwara K., "Enzymatic Processing of Starch: Present and Potential Benefits," Int. Sugar Jnl. vol. 100, p. 372-376. 426-427 (1998).
Starch, vol. 37, p. 92-98 (1992).

* cited by examiner

*Primary Examiner* — Taeyoon Kim
(74) *Attorney, Agent, or Firm* — Occhiuti Rohlicek & Tsao LLP

(57) ABSTRACT

A method for producing a monosaccharide-rich syrup from starch-containing produce. The method includes treating a starch-containing produce slurry with a first starch hydrolyzing enzyme that hydrolyzes starch to oligosaccharide and a second starch hydrolyzing enzyme that hydrolyzes starch or oligosaccharide to glucose. The starch-containing produce can be further treated with an enzyme that converts glucose to other monosaccharides, or treated with a microorganism that converts glucose to a fermentation product. Also within the scope of this invention is a method for producing a syrup rich in a disaccharide, such as trehalose.

4 Claims, No Drawings

STARCH-DERIVED PRODUCTS

RELATED APPLICATION

This application claims priority to U.S. Provisional Application Ser. No. 60/448,814, filed Feb. 19, 2003, the contents of which are incorporated herein by reference.

BACKGROUND

Starch-derived products include sugars and fermentation goods.

A variety of sugars, which find their use in food and pharmaceutical industries, can be prepared from starch. Generally, the starch is first isolated from starch-containing produce by a tedious and costly process. Further, the process involves use of undesirable chemicals.

Fermentation goods such as wine and vinegar also have great commercial value. Traditional production methods require a long fermentation time due to the slow rate of converting starch to fermentable sugars by microorganisms.

Thus, there exists a need to develop better processes for preparing starch-derived products.

SUMMARY

In one aspect, this invention features a method for producing a monosaccharide-rich syrup from starch-containing produce. The method includes treating a starch-containing produce slurry with a first starch hydrolyzing enzyme (e.g., α-amylase, isoamylase, pullulanase, and amylopullulanase) that hydrolyzes starch to oligosaccharide and a second starch hydrolyzing enzyme (e.g., glucoamylase) that hydrolyzes starch or oligosaccharide to glucose. The starch-containing produce slurry can also be treated with a converting enzyme (e.g., glucose isomerase) or a microorganism (e.g., Moniliella PTA-2862) that converts glucose to other monosaccharides.

The term "monosaccharide" mentioned herein refers to saccharides that contain three to seven carbons, including sugars and their derivatives (e.g., sugar alcohols). Examples of a monosaccharide include, but are not limited to, glucose, fructose, sorbose, xylose, mannitol, erythritol, sorbitol, and xylitol. A monosaccharide-rich syrup may contain more than 3% (e.g., 5% or 10%) monosaccharide. The term "converting enzyme" refers to enzymes that convert one saccharide to another saccharide. Both starch hydrolyzing enzymes and converting enzymes can be isolated from different natural sources, such as microorganisms, animals, or plants, or can be prepared by recombinant technology. The term "starch-containing produce" refers to any produce that contains starch. Examples include, but are not limited to, rice, tapioca, grain sorghum, potato, sweet potato, wheat, barley, corn, and legumes. The term "starch-containing produce slurry" refers to a slurry formed by stirring in water starch-containing produce (e.g., milled rice), which has not been chemically or otherwise processed.

An example of practicing the above-described method follows: One first treats a starch-containing produce slurry with α-amylase and then remove insoluble materials from the slurry to obtain a starch hydrolysate-containing solution. The solution thus obtained is subsequently treated with glucoamylase to obtain a glucose-rich syrup. The glucose-rich syrup can be further treated with glucose isomerase to obtain a fructose-rich syrup. Alternatively, the glucose-rich syrup can be treated with a microorganism to obtain a syrup rich in sorbose, xylose, mannitol, erythritol, sorbitol, or xylitol.

In another aspect, this invention features a method for preparing a fermentation product from starch-containing produce. The method includes treating a starch-containing produce slurry with a first starch hydrolyzing enzyme (e.g., α-amylase) that hydrolyzes starch to oligosaccharide, a second starch hydrolyzing enzyme (e.g., glucoamylase) that hydrolyzes starch or oligosaccharide to glucose, and a microorganism (e.g., Aspergillus oryzae) that converts glucose to a fermentation product. The term "fermentation product" refers to any products prepared from glucose by fermentation. Examples include, but are not limited to, wine, vinegar, lactic acid, citric acid, and amino acids. To practice this method, one can first treat a starch-containing produce slurry with α-amylase and then remove insoluble materials from the slurry to obtain a starch hydrolysate-containing solution, then treat the solution with glucoamylase to obtain a glucose-rich syrup, and finally treat the syrup with a microorganism to obtain a fermentation product.

In still another aspect, the invention features a method for producing a trehalose-rich syrup from starch-containing produce. The method includes treating a starch-containing produce slurry with a first starch hydrolyzing enzyme (e.g., α-amylase) that hydrolyzes starch to oligosaccharide, a second starch hydrolyzing enzyme (e.g., β-amylase) that hydrolyzes starch or oligosaccharide to maltose, and a converting enzyme (e.g., trehalose synthase) that converts maltose to trehalose. The second starch hydrolyzing enzyme and the converting enzyme can be the same enzyme. A trehalose-rich syrup may contain more than 0.3% (e.g., 0.5%) trehalose. To practice this method, one can first treat a starch-containing produce slurry with α-amylase and then remove insoluble materials from the slurry to obtain a starch hydrolysate-containing solution, then treat the solution with β-amylase to obtain a maltose-rich syrup, and finally treat the syrup with trehalose synthase to obtain a trehalose-rich syrup.

In a further aspect, the invention features a method for preparing an isomaltose-rich syrup from starch-containing produce. The method includes treating a starch-containing produce slurry with a first starch hydrolyzing enzyme (e.g., α-amylase) that hydrolyzes starch to oligosaccharide, a second starch hydrolyzing enzyme (e.g., β-amylase) that hydrolyzes starch or oligosaccharide to maltose, and a converting enzyme (e.g., α-isomaltosyltransferase) that converts maltose to isomaltose. An isomaltose-rich syrup may contain more than 0.5% isomaltose.

Also within the scope of this invention is a method for culturing a microorganism. The method includes growing the microorganism in a starch hydrolysate-containing solution or a glucose-rich syrup prepared from starch-containing produce by the methods described herein.

The details of one or more embodiments of the invention are set forth in the description below. Other features, objects, and advantages of the invention will be apparent from the description and from the claims.

DETAILED DESCRIPTION

This invention relates to methods for preparing syrups and fermentation products by treating starch-containing produce with enzymes or microorganisms. These enzymes and the microorganisms can be either purchased from a commercial source or prepared by the methods well known in the art.

As one example, one can first treat a starch-containing produce slurry with a thermal stable α-amylase at an elevated temperature to hydrolyze starch to a soluble hydrolysate and to coagulate proteins. A solution containing a starch hydrolysate can be obtained after removing insoluble materials (e.g., coagulated proteins) from the slurry. The starch hydrolysate contains mostly oligosaccharides. The solution thus obtained can be subsequently treated with glucoamylase to obtain a glucose-rich syrup. The yield of the glucose in the syrup may vary depending from the temperature, the pH, the reaction time, and the nature and quantity of the enzymes used in the above processes.

The glucose-rich syrup can be further treated with glucose isomerase to obtain a fructose-rich syrup. The fructose-rich syrup can be used as a sweetener in beverages, baked or canned foods, and dairy products. Other monosaccharides can also be obtained by treating the glucose-rich syrup or the fructose-rich syrup with a microorganism. See, e.g., Lin et al., U.S. Pat. No. 6,455,301 and Ojamo et al., U.S. Pat. No. 6,602,691. Alternatively, the glucose-rich syrup can be treated with a microorganism to obtain a fermentation product, such as wine, vinegar, lactic acid, citric acid, or amino acids. For example, the glucose-rich syrup prepared from rice can be used to produce rice wine directly or can also be mixed with grapes to facilitate the production of red wine. To produce amino acids, one or more nitrogen sources should be present in the glucose-rich syrup. For example, one can add urea to the glucose-rich syrup. 1-Glutamic acid can be produced from glucose using the bacteria *Brevibacterium divaricatum* nov. sp. See, e.g., Su, et al., Bulletin of the Association of Agricultural Chemical Society of Japan, 1960, 24(2):140-146.

A starch hydrolysate-containing solution mentioned above can be further treated with β-amylase to obtain a maltose-rich syrup. The maltose-rich syrup can be treated with trehalose synthase to obtain a trehalose-rich syrup. A trehalose-rich syrup can be used directly as an ingredient in foods. Also, high purity trehalose can be isolated from it for use in pharmaceuticals. The maltose-rich syrup can also be treated with other converting enzymes (e.g., α-isomaltosyltransferase) to obtain a syrup rich in other disaccharides (e.g., isomaltose). Alternatively, the starch hydrolysate-containing solution can be treated with an enzyme that has the functions of both β-amylase and trehalose synthase to obtain a trehalose-rich syrup directly from the starch hydrolysate-containing solution. This enzyme can be prepared by standard recombinant technology.

The above-described reactions can be conducted either continuously (in a reactor containing immobilized enzymes or microorganisms) or discontinuously (via a batch process). Either free or immobilized enzymes or microorganisms may be used to practice the methods of this invention. The enzymes or the microorganisms can be added sequentially or simultaneously. Preferably, different enzymes or microorganisms are used separately under optimal operative conditions.

The insoluble materials mentioned above can be removed either before or after a syrup or a fermentation product is formed. The removal process can be carried out by filtration, centrifugation, and decantation.

The yields and compositions of the sugars and fermentation products prepared by the methods of this invention can be determined by suitable analytical methods, such as high-performance liquid chromatography and gas chromatography.

The starch hydrolysate-containing solution and the glucose-rich syrup obtained above can be used to as culture media to grow microorganisms. They can be used as is, or, they can be dried first and then dissolved in a solution containing other ingredients before use.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Preparation of a Glucose-Rich Syrup

Milled rice (*Oryza sativa* L.) of Tainung 67 cultivar was obtained from Taichung Agricultural Experimental Station (Changhua, Taiwan). Thermostable α-amylase (120 U/g, 1.20 g/mL; TERMAMYL 120 L) was obtained from Novo Nordisk Biochem (Bagsvaerd, Denmark). *Rhizopus* sp. glucoamylase (5,000 units/g solid) was obtained from Sigma Chemical Co. (St. Louis, Mo.). Standard samples of glucose, fructose, trehalose, and ethanol were obtained from Sigma Chemical Co. The concentrations of glucose in the syrup obtained were measured by high-performance liquid chromatography (a HITACHI L6250 HPLC system equipped with BISCHOFF RI detector) at a flow rate of 1 mL/min on a ThermoHyoersil HS APS2 column (particle size, 5 μm; 250× 4.6 mm). The mobile phase was acetonitrile/distilled water/formic acid (80:20:1). The presence of the glucose was confirmed by comparing the retention times with those of the standard samples (e.g., 7.75 minutes for glucose, 12.21 minutes for maltose, and 13.7 minutes for trehalose).

A slurry containing 10% rice flour (>100 mesh) in deionized water was thoroughly mixed with thermostable α-amylase (0.1% of dry solid) at 90° C. The starch was hydrolyzed into soluble hydrolysate, which was monitored by calorimetric methods based on the formation of amylose-iodine complex. All the proteins in the rice flour were essentially heat-coagulated by this process and precipitated from the starch hydrolysate solution. The precipitate was collected by filtration and dried to give high-protein rice flour. About 0.9 g of the soluble starch hydrolysate and about 0.1 g of high-protein rice flour was produced from 1 g of dry rice under the above-mentioned conditions.

The starch hydrolysate (containing mostly oligosaccharide mixtures, DP≧7) was further treated with *Rhizopus* sp. glucoamylase to produce the high-glucose syrup. Specifically, *Rhizopus* sp. glucoamylase (0.5 mg/mL) was added to the soluble starch hydrolysate and incubated at 55° C. In the absence of glucoamylase, the glucose concentration of the solution remained 11 mg/mL after 150 minutes. By contrast, in the presence of glucoamylase, the glucose concentration increased rapidly to 105 mg/mL in 60 minutes and reached the maximum concentration 114 mg/mL in 120 minutes.

Example 2

Preparation of a Fructose-Rich Syrup

Glucose isomerase (SWEETZYMEE) can be obtained from Novo Nordisk Biochem (Bagsvaerd, Denmark). The sources of other materials and the conditions of the instruments used in this example are described in Example 1 above. A fructose-rich syrup is prepared by treating a glucose-rich syrup obtained in Example 1 above with glucose isomerase. The concentrations of fructose are measured in a manner similar to that of glucose.

Example 3

Preparation of a Trehalose-Rich Syrup

β-Amylase Type I-B from sweet potato (ammonium sulfate suspension, 980 units/mg protein) was obtained from Sigma Chemical Co. (St. Louis, Mo.). Recombinant *Deinococcus radiodurans* trehalose synthase was heterologously expressed from *Escherichia coli* BL21(DE3). The sources of other materials and the conditions of the instruments used in this Example are described in Example 1 above. The concentrations of trehalose were measured in a manner similar to that of glucose.

The starch hydrolysate obtained above (maltose concentration: 34 mg/mL) was saccharified using β-amylase (25 µg/mL) from sweet potato at 55° C. for 10 minutes to obtain a syrup rich in maltose (maltose concentration: 77 mg/mL). The syrup thus obtained was further treated with recombinant trehalose synthase (75 µg/mL) from *Deinococcus radiodurans* at 15° C. The concentration of trehalose reached 12 mg/mL in 60 minutes. By contrast, without the treatment of β-amylase, the concentration of trehalose was only 5 mg/mL during the same period of time. In other words, the β-amylase treatment, which enriched maltose (the substrate for trehalose), unexpectedly increased the yield of trehalose by 2.4 folds.

Example 4

Preparation of Rice Wine

*Aspergillus oryzae* CCRC30884 was purchased from the Bioresource Collection and Research Center (Hsinchu, Taiwan). The sources of other materials and the conditions of the instruments used in this Example are described in Example 1 above unless otherwise specified.

*Aspergillus oryzae* (10 mg/mL) was added to the syrup rich in glucose obtained in Example 1 (glucose concentration: 105 mg/mL) under anaerobic condition at 30° C. The concentrations of ethanol in the fermentation products were measured by gas chromatography. Quantitative analysis was carried out on a Hitachi gas chromatograph model G-3000 equipped with a flame ionization detector. Ethanol produced by fermentation was separated on a RTX-1 cross-linked 100% dimethyl polysiloxane capillary column (30 m×0.25 mm×0.25 µm; RESTEK Corp., Bellefonte, Pa.) using nitrogen as the carrier gas at a flow rate of 1.0 mL/min. The split ratio was 1:10. The temperatures of the injector and the flame ionization detector were both at 200° C. The column temperature was held at 90° C. for 6 minutes. The retention time for ethanol was 2.28 minutes. Peak areas were calculated using a Hitachi integrator (model D-2000).

The results show that the ethanol concentration unexpectedly increased to 10.5% after fermentation in only three days and reached 13.5% after fermentation in only five days. By contrast, only 1% of ethanol was produced from the original starch hydrolysate (glucose concentration: 11 mg/mL) under the same fermentation conditions after 5 days.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for producing a fermentation product from starch-containing produce, the method comprising:
   treating a starch-containing produce slurry containing 10% rice flour with a first starch hydrolyzing enzyme that hydrolyzes starch to oligosaccharide at a temperature under which protein coagulates, the first being a thermal stable α-amylase,
   removing insoluble materials from the slurry to obtain a starch hydrolysate-containing solution,
   treating the starch hydrolysate-containing solution with a second starch hydrolyzing enzyme that hydrolyzes starch or oligosaccharide to glucose to obtain a glucose-rich syrup containing 105 mg/ml or 114 mg/ml glucose, the second starch hydrolyzing enzyme being glucoamylase, and
   growing *Aspergillus oryzae* in the glucose-rich syrup as is for three days to produce a fermentation product containing 10.5% ethanol, or for five days to produce a fermentation product containing 13.5% ethanol.

2. The method of claim 1, wherein the fermentation product is wine.

3. The method of claim 1, wherein the temperature is 90° C.

4. The method of claim 2, wherein the temperature is 90° C.

* * * * *